(12) United States Patent
Kelly et al.

(10) Patent No.: US 10,080,888 B2
(45) Date of Patent: Sep. 25, 2018

(54) INTERVENTIONAL MEDICAL SYSTEMS AND ASSOCIATED METHODS

(71) Applicant: Medtronic, Inc., Minneapolis, MN (US)

(72) Inventors: Tomas K Kelly, Galway (IE); Gwenda Francis, Galway (IE); Brendan P Geraghty, Galway (IE); Pat McHugh, Ballyhaunis (IE); Sean Ward, Dublin (IE)

(73) Assignee: Medtronic, Inc., Minneapolis, MN (US)

( * ) Notice: Subject to any disclaimer, the term of this patent is extended or adjusted under 35 U.S.C. 154(b) by 359 days.

(21) Appl. No.: 14/942,609

(22) Filed: Nov. 16, 2015

(65) Prior Publication Data

US 2017/0136231 A1 May 18, 2017

(51) Int. Cl.
*A61B 19/00* (2006.01)
*A61N 1/05* (2006.01)
*A61M 25/00* (2006.01)
*A61M 25/01* (2006.01)
*A61N 1/375* (2006.01)
(Continued)

(52) U.S. Cl.
CPC ......... *A61N 1/059* (2013.01); *A61M 25/0074* (2013.01); *A61M 25/0108* (2013.01); *A61M 25/0147* (2013.01); *A61N 1/0573* (2013.01); *A61N 1/0587* (2013.01); *A61N 1/3756* (2013.01); *A61N 1/37205* (2013.01); *A61N 1/0575* (2013.01); *A61N 1/086* (2017.08)

(58) Field of Classification Search
CPC .. A61B 17/3468; A61N 1/056; A61N 1/0565; A61N 1/0573; A61N 1/0575; A61N 1/0587; A61N 1/059; A61N 1/086; A61N 1/37205; A61N 2001/0578; A61N 2001/058
USPC ........................................................ 606/129
See application file for complete search history.

(56) References Cited

U.S. PATENT DOCUMENTS

| 2,114,695 | A | 4/1938 | Anderson |
| 3,835,864 | A | 9/1974 | Rasor et al. |
| 4,655,219 | A | 4/1987 | Petruzzi |

(Continued)

OTHER PUBLICATIONS (PCT/US2016/038609) PCT Notification of Transmittal of the International Search Report and the Written Opinion of the International Searching Authority, dated Aug. 29, 2016, 10 pages.
(Continued)

*Primary Examiner* — Melanie Tyson

(57) ABSTRACT

A shaft of an interventional medical system catheter has a distal end formed by opposing elastically deformable retention features that protrude into a lumen of the shaft, and that define an expandable distal opening of the lumen. The retention features secure an implantable medical device to the catheter by an interlocking engagement within a gap defined by a necked-in portion of a device holding member. Each retention feature includes a distal-facing surface defining the distal opening, and, when an elongate release member of the catheter, which extends within the shaft lumen, applies a push force against proximal-facing surfaces of the features, the distal opening expands from a constricted to an open configuration, wherein the open configuration allows passage of the device holding member through the distal opening, and the constricted configuration allows for the interlocking engagement with the device.

14 Claims, 11 Drawing Sheets

(51) Int. Cl.
*A61N 1/372* (2006.01)
*A61N 1/08* (2006.01)

(56) References Cited

U.S. PATENT DOCUMENTS

| | | | |
|---|---|---|---|
| 4,710,181 | A | 12/1987 | Fuqua |
| 5,026,377 | A | 6/1991 | Burton et al. |
| 5,171,233 | A | 12/1992 | Amplatz et al. |
| 5,234,437 | A | 8/1993 | Sepetka |
| 5,350,397 | A | 9/1994 | Palermo et al. |
| 5,417,697 | A | 5/1995 | Wilk et al. |
| 5,476,510 | A | 12/1995 | Eberhardt et al. |
| 6,156,055 | A | 12/2000 | Ravenscroft |
| 6,187,016 | B1 | 2/2001 | Hedges et al. |
| 6,277,125 | B1 | 8/2001 | Barry et al. |
| 6,348,056 | B1 | 2/2002 | Bates et al. |
| 6,355,060 | B1 | 3/2002 | Lenker et al. |
| 6,501,993 | B2 | 12/2002 | Morgan et al. |
| 6,506,205 | B2 | 1/2003 | Goldberg et al. |
| 6,846,317 | B1 | 1/2005 | Nigon |
| 6,953,473 | B2 | 10/2005 | Porter |
| 7,033,376 | B2 | 4/2006 | Tsukernik |
| 7,323,003 | B2 | 1/2008 | Lowe |
| 8,025,668 | B2 | 9/2011 | McCartney |
| 8,364,280 | B2 | 1/2013 | Marnfeldt et al. |
| 8,777,932 | B2 | 7/2014 | Sage et al. |
| 8,945,145 | B2 | 2/2015 | Tran et al. |
| 9,237,948 | B2 | 1/2016 | Colson et al. |
| 9,480,850 | B2 | 11/2016 | Schmidt et al. |
| 9,700,732 | B2 | 7/2017 | Schmidt et al. |
| 9,775,636 | B2 | 10/2017 | Fazio et al. |
| 9,844,664 | B2 | 12/2017 | McEvoy et al. |
| 2005/0159771 | A1 | 7/2005 | Petersen |
| 2006/0085041 | A1 | 4/2006 | Hastings et al. |
| 2006/0247572 | A1 | 11/2006 | McCartney |
| 2007/0005131 | A1 | 1/2007 | Taylor |
| 2008/0065011 | A1 | 3/2008 | Marchand et al. |
| 2009/0182370 | A1 | 7/2009 | Volobuyev et al. |
| 2012/0165827 | A1 | 6/2012 | Khairkhahan et al. |
| 2012/0172690 | A1 | 7/2012 | Anderson et al. |
| 2012/0172891 | A1 | 7/2012 | Lee |
| 2012/0184987 | A1 | 7/2012 | Sirota |
| 2012/0239130 | A1 | 9/2012 | Hartley et al. |
| 2013/0053921 | A1 | 2/2013 | Bonner et al. |
| 2013/0103047 | A1 | 4/2013 | Steingisser et al. |
| 2013/0131591 | A1 | 5/2013 | Berthiaume et al. |
| 2014/0142621 | A1 | 5/2014 | Masters et al. |
| 2014/0163579 | A1 | 6/2014 | Tischendorf et al. |
| 2015/0051609 | A1 | 2/2015 | Schmidt et al. |
| 2015/0051610 | A1 | 2/2015 | Schmidt et al. |
| 2015/0051611 | A1 | 2/2015 | Schmidt et al. |
| 2015/0094668 | A1 | 4/2015 | Wood et al. |
| 2015/0094735 | A1 | 4/2015 | Ward et al. |
| 2015/0273212 | A1 | 10/2015 | Berthiaume et al. |
| 2016/0015968 | A1 | 1/2016 | Bonner et al. |
| 2016/0015983 | A1 | 1/2016 | Sheldon et al. |
| 2016/0143661 | A1 | 5/2016 | Wood et al. |
| 2016/0243355 | A1 | 8/2016 | Wood |
| 2017/0028190 | A1 | 2/2017 | O'Carroll et al. |
| 2017/0100582 | A1 | 4/2017 | McEvoy et al. |

OTHER PUBLICATIONS (PCT/US2016/061863) PCT Notification of Transmittal of the International Search Report and the Written Opinion of the International Searching Authority, dated Jan. 31, 2017, 11 pages.

NOVA® Optional Accessories (1 page), accessed Nov. 16, 2015, http://www.panamericantool.com/9-32-40-aircraft-collets.html.

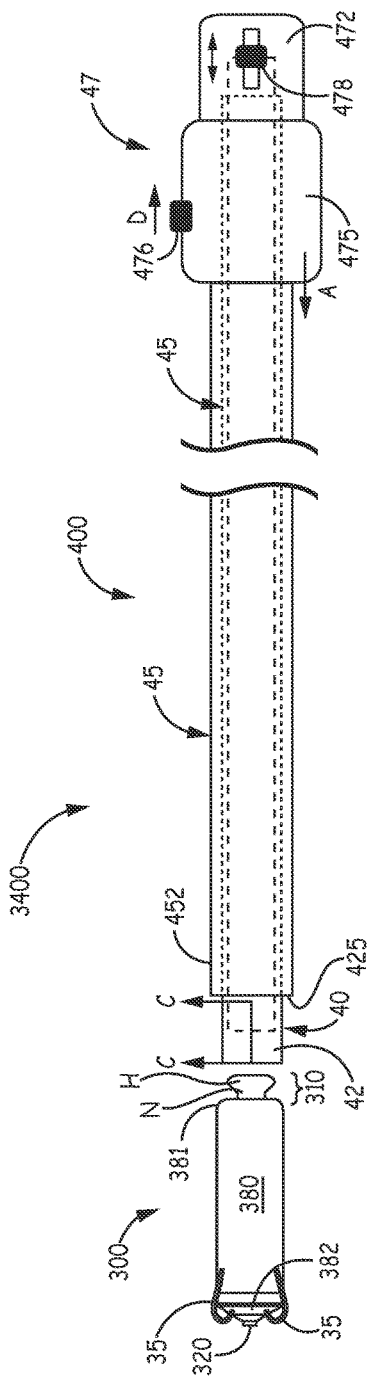
FIG. 3A
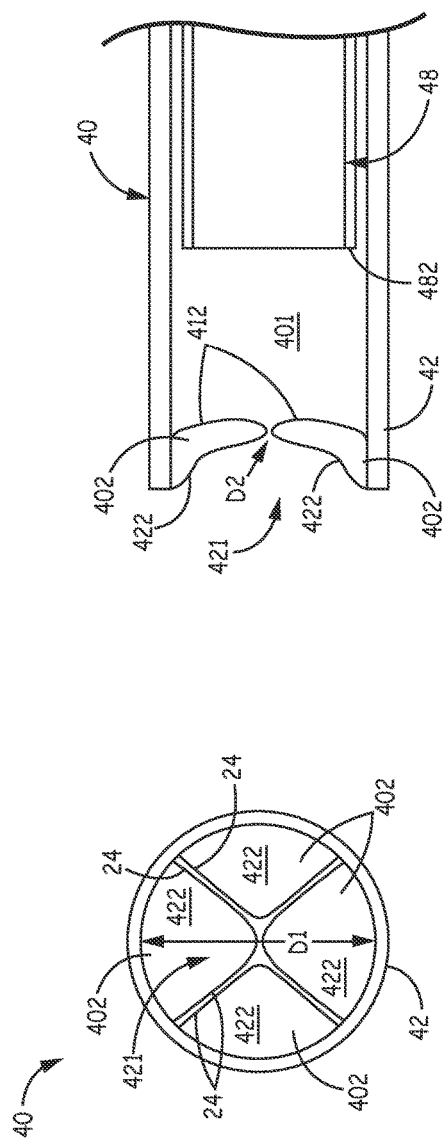
FIG. 3C
FIG. 3B

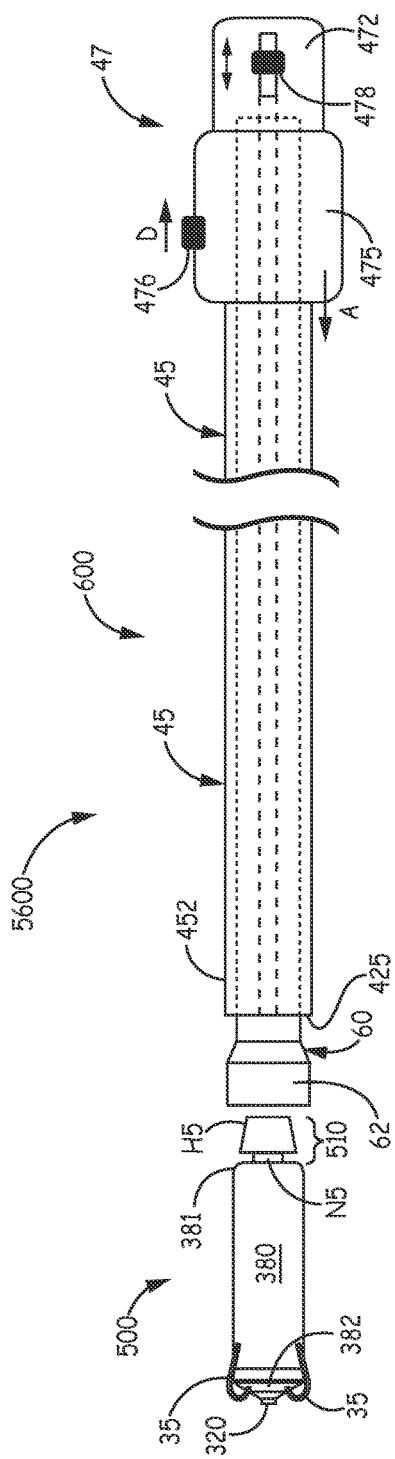
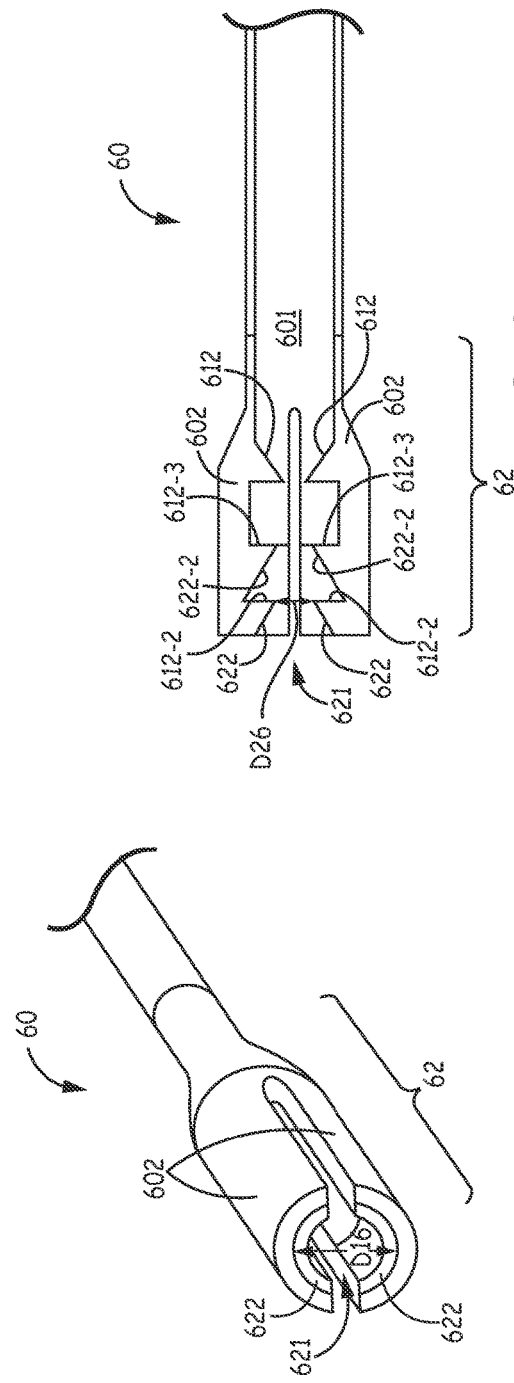
FIG. 5A
FIG. 5B
FIG. 5C

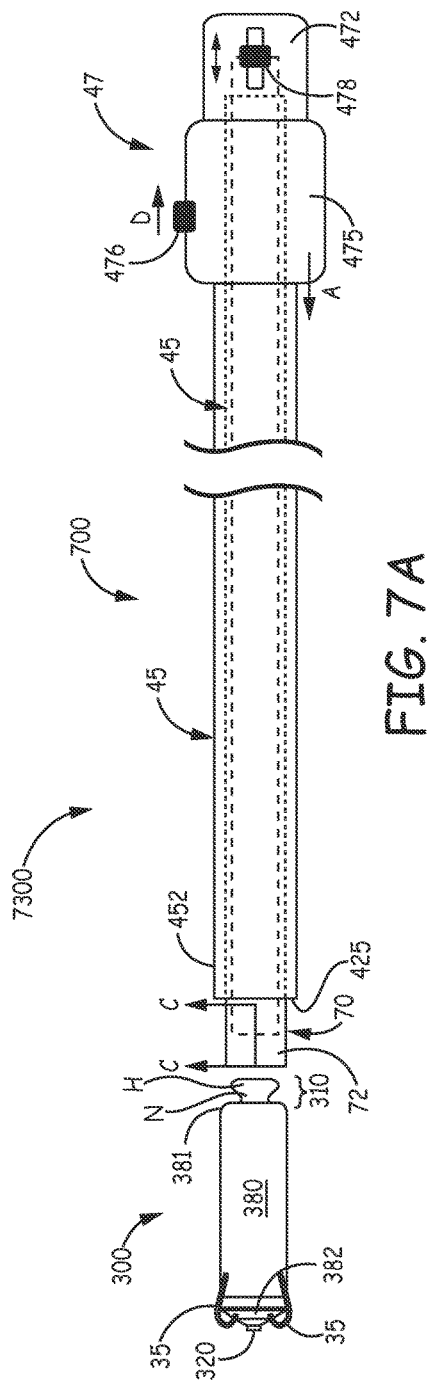
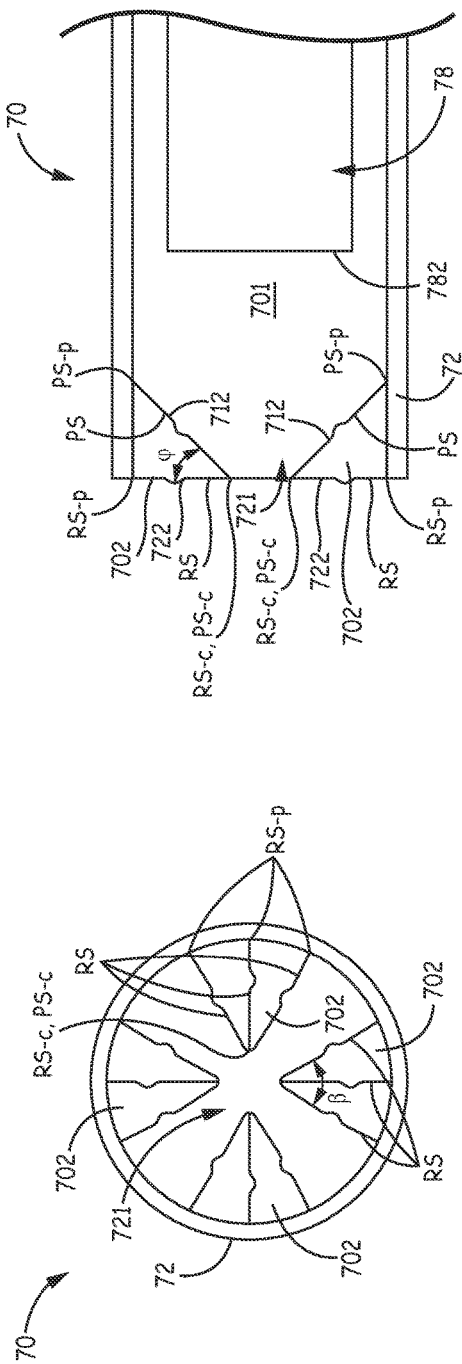
FIG. 7A
FIG. 7B
FIG. 7C

INTERVENTIONAL MEDICAL SYSTEMS AND ASSOCIATED METHODS

FIELD OF THE DISCLOSURE

The present disclosure pertains to interventional medical systems, and more particularly to those that include relatively compact medical devices and catheters that are useful for delivering and retrieving the devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 illustrates an exemplary relatively compact implantable medical device 100 having been delivered through a catheter 200, which an operator has maneuvered up through the inferior vena cava IVC and the right atrium RA into the right ventricle RV. Device 100 and catheter 200 may be similar to the device and tool, respectively, described in the commonly assigned United States Patent Application US 2015/0094668. Device 100 is shown fixed at an implant site by a fixation member 115 thereof, but still secured to catheter 200 by a flexible tether 280 that extends out from distal opening 203 of catheter 200, being joined to a holding member 121 of device 100. Thus, the operator, via tether 280, is able to test the fixation of device 100 at the implant site, and/or remove device 100 from the implant site for repositioning at a more suitable site, if necessary. Once satisfied with the implant of device 100, the operator can separate tether 280 from device 100, for example, by releasing an end of one length 281 of tether 280, and then pulling on an end of another length 282 of tether 280 to withdraw an entirety of length 282 proximally through delivery catheter 200 so that tether length 281 is pulled distally and through device holding member 121. If the operator subsequently desires to retrieve device 100 from the implant site, a snare tool may be employed in conjunction with catheter 200, wherein the operator may "lasso" device holding member 121 with a snare loop of the tool, according to methods known in the art.

Securing device 100 to catheter 200 with tethering member 280 is typically accomplished by a process in which tethering member 280 is looped through device holding member 121, after which first and second lengths 281, 282 of tether 280 are threaded through one or more lumens of catheter 200 such that opposing ends thereof protrude out from a proximal opening 201 of catheter 200. Because this process may be somewhat tedious a manufacturer of device 100 and catheter 200 may secure the two together as a system, and provide the system to the operator in a single sterile package. However, due to shelf life considerations, the packaging of such a device separately from the associated catheter may be preferred, so that alternative means for securing the device to the catheter may be necessary to increase the ease by which an operator may load the device into the catheter at the time of an implant procedure. Additionally, improvements to these systems that increase the ease and efficiency of retrieving the medical device from an implant site may also be desired.

SUMMARY

Embodiments of interventional medical systems, disclosed herein, include a relatively compact implantable medical device and an associated catheter, wherein a shaft of the catheter has a distal end formed by opposing elastically deformable retention features. The retention features protrude into a lumen of the shaft, define an expandable distal opening of the shaft lumen, and are configured to secure the device to the catheter by an interlocking engagement within a gap defined by a necked-in portion of a holding member of the device, which is joined to a proximal end of a housing of the device. According to some embodiments, each of the opposing elastically deformable retention features include a proximal-facing surface and a distal-facing surface, wherein the distal-facing surfaces define the distal opening of the catheter shaft lumen, which is expandable from a constricted configuration to an open configuration in response to deformation of the retention features, for example, when an elongate release member of the catheter, which extends within the shaft lumen, applies a push force against the proximal-facing surfaces of the retention features. The open configuration allows passage of the device holding member through the distal opening of the shaft lumen, and the constricted configuration allows for the aforementioned interlocking engagement of the retention features with the device. In some embodiments, the distal opening of the catheter shaft lumen may taper from a first, distal-most diameter to a second diameter, wherein the second diameter of the distal opening is less than the first diameter, and expands from the constricted configuration to the open configuration.

According to some methods, an operator loads the device into the catheter by bringing the device holding member into confronting engagement with the opposing retention features of the catheter shaft, and then pushing the confronting device holding member and the catheter shaft retention features against one another to elastically deform the opposing retention features and expand the distal opening of the shaft lumen, and to pass the device holding member through the expanded distal opening and into the lumen, so that the retention features come into the interlocking engagement within the gap defined by the necked-in portion of the holding member. The loaded device may then be delivered to an implant site in a patient's vascular system by advancing the catheter within the vascular system so that a fixation member of the device, which is mounted to a distal end of the device housing, is positioned in close proximity to the implant site, and then by engaging the positioned device fixation member with tissue at the implant site by applying a push force through the catheter shaft. After the operator engages the device fixation member, the operator can release the device from the interlocking engagement of the catheter shaft retention features by applying a push force, with the release member, against the proximal-facing surfaces of the retention features, thereby elastically deforming the retention features and expanding the distal opening of the lumen.

In some methods, if the operator determines that the implanted device needs to be retrieved from the implant site, for example, to be repositioned at another implant site, the operator can apply the push force through the release member of the catheter to elastically deform the retention features and expand the distal opening of the catheter shaft lumen, and then position the expanded distal opening around the holding member of the implanted device. After positioning the expanded distal opening, the operator can retract the release member, thereby allowing the distal opening of the catheter shaft lumen to constrict so that the retention features interlock within the gap defined by the necked-in portion of the device holding member, and then apply a pull force through the catheter shaft to disengage the device fixation member from tissue at the implant site.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 3A is a plan view of an interventional medical system, according to some embodiments of the present invention;

FIG. 3B is a distal end view of an inner assembly of a catheter of the FIG. 3A system, according to some embodiments;

FIG. 3C is a longitudinal cross-section view, per section line C-C of FIG. 3A, according to some embodiments;

FIG. 5A is a plan view of an interventional medical system, according to some alternate embodiments of the present invention;

FIG. 5B is a perspective view of a distal portion of an inner assembly of a catheter of the FIG. 5A system;

FIG. 5C is a longitudinal cross-section view through the distal portion of FIG. 5B, according to some embodiments;

FIG. 7A is a plan view of an interventional medical system, according to some additional embodiments of the present invention;

FIG. 7B is a distal end view of an inner assembly of a catheter of the FIG. 7A system, according to some embodiments;

FIG. 7C is a longitudinal cross-section view, per section line C-C of FIG. 7A, according to some embodiments;

DETAILED DESCRIPTION

Figure 1:
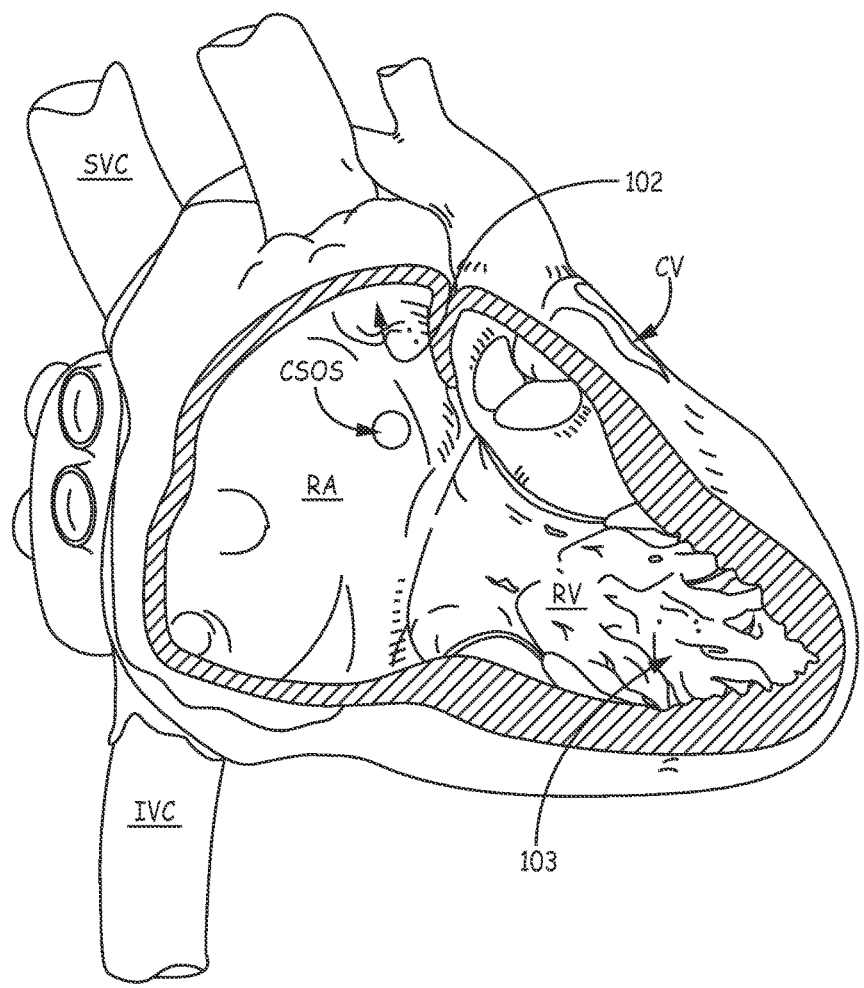
FIG. 1 is a schematic diagram showing potential implant sites for a relatively compact implantable medical device.
Figure 2:
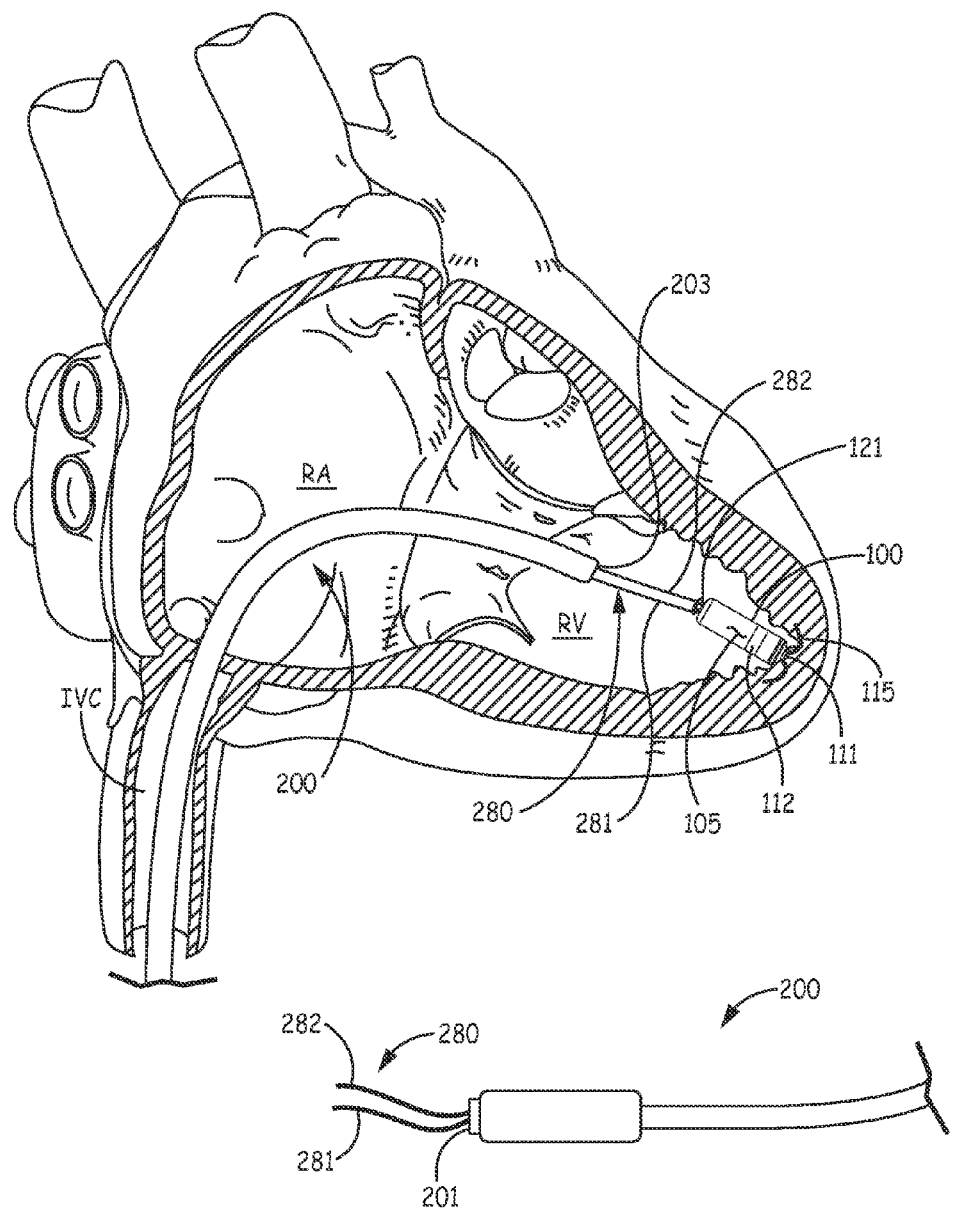
FIG. 2 is a schematic showing an exemplary relatively compact implantable medical device having been delivered from a catheter to an implant site.

The following detailed description is exemplary in nature and is not intended to limit the scope, applicability, or configuration of the invention in any way. Rather, the following description provides practical examples, and those skilled in the art will recognize that some of the examples may have suitable alternatives.

FIG. 3A is a plan view of an interventional medical system 3400, according to some embodiments of the present invention. A relatively compact implantable medical device 300 of system 3400 is shown positioned for loading into a catheter 400 of system 3400. FIG. 3A illustrates catheter 400 including a shaft 40, which is part of an inner assembly of catheter 400, an elongate outer tubular member 45, and a handle 47, which has a distal portion 475 coupled to a proximal end of outer tubular member 45, and a proximal portion 472 coupled to a proximal end of inner assembly shaft 40. Although not shown, it should be understood that outer tubular member 45 includes an elongate lumen that extends along a length of tubular member 45, from the proximal end thereof, formed in handle distal portion 475, to a distal end 452 thereof; and that the inner assembly of catheter 400 extends along and is in sliding engagement within the lumen of outer tubular member 45. In FIG. 3A, the extent of the inner assembly is shown with dotted lines and dashed lines. According to the illustrated embodiment, outer tubular member 45 is movable, via handle distal portion 475, relative to the inner assembly, between a retracted position, at which a distal end 42 of inner assembly shaft 40 is exposed distal to a distal-most opening 425 of the lumen of outer tubular member 45, as shown in FIG. 3A, and an advanced position, at which distal end 42 is contained within the lumen of outer tubular member 45, for example, when medical device 300 is loaded into catheter 400, as is described below in conjunction with FIGS. 4A-C and 7A.

In some exemplary embodiments, outer tubular member 45 of catheter 400, for example, extending over a length of approximately 100 cm, may be formed by a stainless steel braid-reinforced medical grade polymer, for example, one or more appropriate grades of polyether block amide, which are arranged for decreasing stiffness from handle 47 to a distal end 452 of tubular member 45 (e.g., including PEBAX® 3533, 6333, 4033, and 7233), and tubular member 45 may have a lumen diameter of approximately 0.3 inch (7.6 mm) in proximity to distal-most opening 425, to contain medical device 300 therein. Distal end 452 may have a radiopaque filler blended therein, or a radiopaque marker (e.g., Tungsten-filled Vestamid®) bonded thereto, either according to methods known to those skilled in the art. Inner assembly shaft 40 may be formed from a stainless steel braid-reinforced medical grade polymer, for example, one or more appropriate grades of polyether block amide, which are arranged for decreasing stiffness from a proximal end of shaft 40 to distal end 42 (e.g., PEBAX® 3533, 6333, 4033, and 7233), and shaft 40 may include a fluoropolymer liner, for example, PTFE. With further reference to FIG. 3A, a control member 476 for an optional steering assembly of catheter 400 is shown being mounted to handle distal portion 475. The steering assembly, according to configurations known in the art, may further include a pull band mounted in distal end 452 and an elongate pull wire that extends along a length of tubular member 45, being coupled at a distal end thereof to the pull band and, at a proximal end thereof, to control member 476, such that moving control member 476, per arrow D, causes the pull wire to deflect outer tubular member 45, along with the inner assembly of catheter 400, which may be useful in navigating catheter 400 into proximity with an implant site. Handle 47 may be constructed from injection molded, relatively hard, medical grade plastic parts, according to methods known in the art.

Figure 9A:
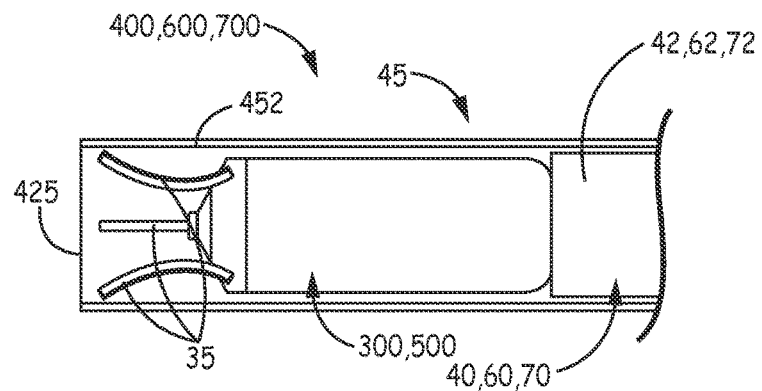
FIGS. 9A-C and 10 are schematics outlining some methods of the present invention.

FIG. 3A further illustrates medical device 300 including a hermetically sealed housing 380, which extends from a proximal end 381 thereof to a distal end 382 thereof, and an electrode 320, which is mounted to housing distal end 382. According to the illustrated embodiment, an electronic controller (not shown), for example, a pulse generator and an associated power supply, are contained within housing 380, and electrode 320 is electrically coupled to the controller via a hermetically sealed feedthrough assembly (not shown) such as is known in the art. Device 300 further includes a fixation member, for example, formed by a plurality of super-elastic fingers 35 spaced apart from one another around a perimeter of housing distal end 382. Although only two fixation fingers 35 are shown in FIG. 3A, device 300 may include as many as eight. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation fingers 35 may be mounted to distal end 382 of device housing 380, for example, in a manner similar to that described for a fixation component 102 in a commonly assigned United States Patent Application 2012/0172690, which description is hereby incorporated by reference. The super-elastic nature of Nitinol allows fingers 35 to elastically deform between a relaxed condition, which is shown, and an extended condition, in which a free end of each finger extends distally away from distal end 382 of device housing 380, for example, when device 300 is loaded into catheter 400, as shown in FIG. 9A.

According to the illustrated embodiment, fixation fingers 35 are configured to pierce into tissue at the implant site and thereby secure electrode 320 in intimate tissue contact. In some embodiments, device 300 preferably includes a steroid-eluting member (not shown), for example, mounted in, or around electrode 320, which is useful for reducing inflammation of the pierced tissue to maintain effective and efficient pacing via electrode 320.

Device housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing. FIG. 3A further illustrates device 300 including a holding member 310 joined to housing proximal end 381 and protruding proximally therefrom. Device holding member 310 is shown including a head H and a necked-in portion N that defines a gap between head H and device housing proximal end 381. FIG. 3A shows medical device 300 oriented so that holding member 310 is directed toward distal end 42 of catheter inner assembly shaft 40 for engagement therewith in the loading of device 300 into catheter 400.

The distal end view of FIG. 3B and the longitudinal cross-section view of FIG. 3C illustrate shaft distal end 42 including opposing elastically deformable retention features 402 that protrude into a lumen 401 of shaft 40, wherein each retention feature 402 includes a proximal-facing surface 421 and a distal-facing surface 422. FIG. 3B illustrates two pairs of opposing retention features 402, according to some embodiments, wherein each feature 402 has a leaflet-type structure, and free edges 24 of adjacent features 402 extend alongside and in close proximity to one another within shaft lumen 401. Distal-facing surfaces 422 are shown defining a distal opening 421 of shaft lumen 401, wherein opening 421 tapers from a first, distal-most diameter D1 to a second diameter D2, which is less than first diameter D1, but is expandable to an open configuration that allows passage of device holding member 310 through distal opening 421, as described below in conjunction with FIGS. 4A-C. According to some embodiments, each retention feature 402 may include an internal structure similar in construction to retention features 702 described below in conjunction with FIGS. 7A-E, wherein an elastic body, for example, a medical grade elastomer such as silicone rubber, encases the structure.

Figure 4A:
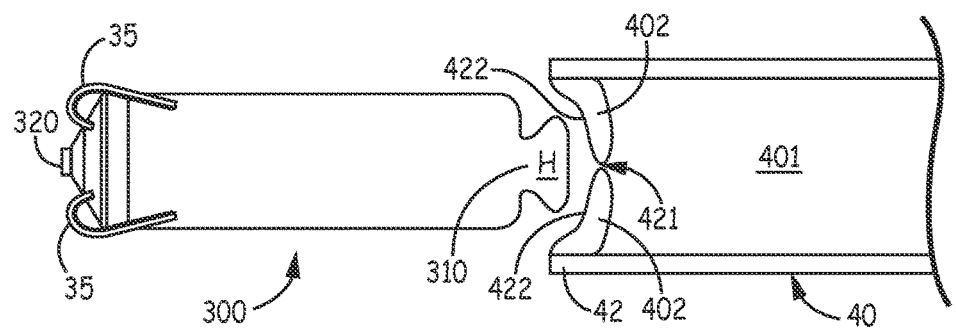
FIGS. 4A-C are plan views, with partial cross-sections, of an exemplary relatively compact medical device of the FIG. 3A system, and a distal end of the catheter inner assembly of the system, according to some embodiments and methods.
Figure 4B:
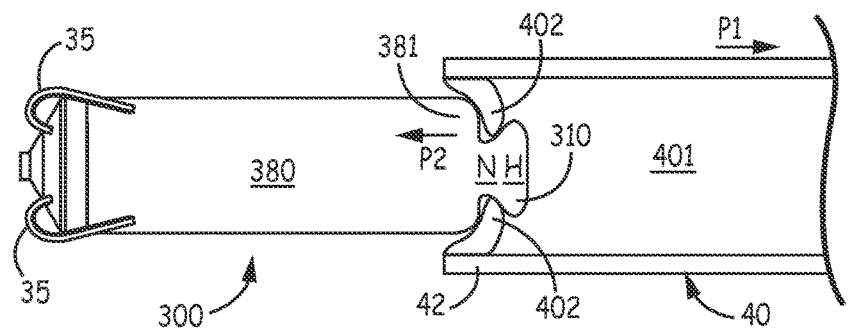

According to the illustrated embodiment, second diameter D2 of shaft lumen distal opening 421 is in a constricted configuration (FIGS. 3B-C) when retention features 402 are in a relaxed condition. To load device 300 into catheter 400, an operator may bring device holding member 310 into confronting engagement with retention features 402, as illustrated in FIG. 4A, and then push holding member 310 and retention features 402 against one another to elastically deform features 402 and expand second diameter D2 of distal opening 421 so that holding member 310 passes therethrough. Once holding member head H passes through distal opening 421, retention features 402 relax back toward the constricted configuration that allows for an interlocking engagement of features 402 within the gap defined by necked-in portion N of device holding member 310, as illustrated in FIG. 4B. With reference back to FIG. 3A, to complete the loading of device 300 into catheter 400, the operator may advance outer tubular member 45, for example, by moving handle distal portion 475 per arrow A, relative to the catheter inner assembly, so that distal end 452 of outer tubular member 45 contains distal end 42 of the catheter inner assembly and the engaged device 300, for example, as shown in FIG. 9A.

Figure 4C:
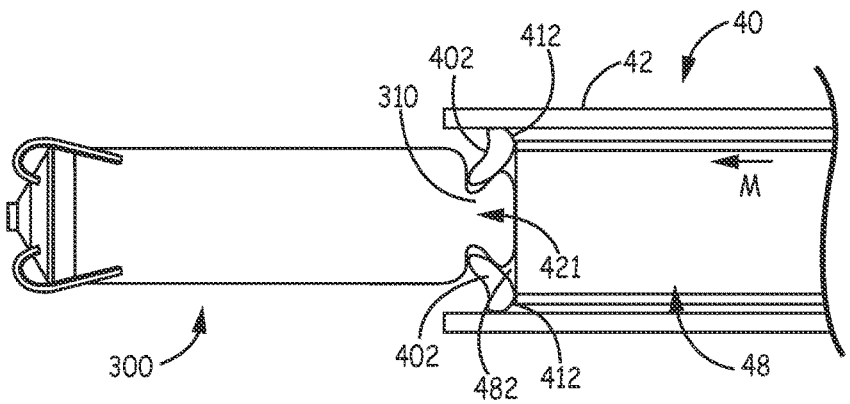

With reference to FIGS. 3C and 4C, catheter 400 further includes an elongate release member 48 configured to slide within shaft lumen 401 and to apply a push force against proximal-facing surfaces 412 of retention features 402. With reference to FIG. 3A, in which release member 48 is represented with dashed lines, a proximal end of release member 48 may be coupled to a control member 478, which is shown mounted to handle proximal portion 472, being movable in proximal and distal directions per the double-headed arrow. According to the illustrated embodiment, retention features 402 are configured to resist deformation in a distal direction in response to a pull force applied through shaft 40, to the engaged device, per arrow P1, or by the engaged device 300, per arrow P2 (FIG. 4B), but the operator may release medical device 300 from the interlocking engagement of shaft distal end 42 by moving member 48 distally within shaft lumen 401, per arrow M, to apply a push force against proximal-facing surfaces 412 of retention features 402, as shown in FIG. 4C. FIGS. 3C and 4C illustrate elongate release member 48 being formed by a tube having a distal-most edge 482 configured to push against proximal-facing surfaces 412 of retention features 402 at a location in relatively close proximity to an inner surface of shaft 40 that defines lumen 401. The push force moves features 402 into a deformed condition at which second diameter D2 of distal opening 421 expands to the open configuration, as shown in FIG. 4C, to allow distal passage of device holding member 310 through distal opening 421.

FIG. 5A is a plan view of an interventional medical system 5600, according to some alternate embodiments, wherein a relatively compact implantable medical device 500 of system 5600 is positioned for loading into a catheter 600 of system 5600. Medical device 500 is shown including many elements that are similar to those described above for device 300. Furthermore, FIG. 5A illustrates catheter 600 including elongate outer tubular member 45 and handle 47, like catheter 400 described above, but an inner assembly of catheter 600 differs from that described above. FIG. 5A illustrates a distal end 62 of a shaft 60 of the inner assembly of catheter 600 exposed distal to distal-most opening 425 of outer tubular member 45. FIG. 5B is a perspective view of a distal portion of the inner assembly of catheter 600; and FIG. 5C is a longitudinal cross-section view through the distal portion, according to some embodiments. FIGS. 5B-C illustrate distal end 62 of shaft 60 of the inner assembly of catheter 500 including formed by opposing elastically deformable retention features 602 that protrude into a lumen 601 of shaft 60. FIGS. 5B-C further illustrate a first distal-facing surface 622 of each retention feature 602 defining a distal opening 621 into shaft lumen 601, wherein distal opening 621 tapers from a first, distal-most diameter D16 to a second diameter D26, which is less than first diameter D16, and is shown in a constricted configuration, according to a relaxed condition of opposing retention features 602.

Figure 6A:
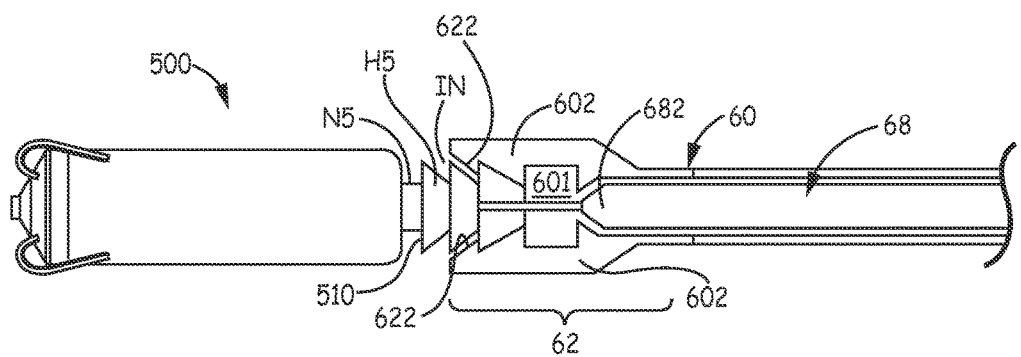
FIGS. 6A-C are plan views, with partial cross-sections, of an exemplary relatively compact medical device of the FIG. 5A system, and a distal end of the catheter inner assembly of the system, according to some embodiments and methods.
Figure 6B:
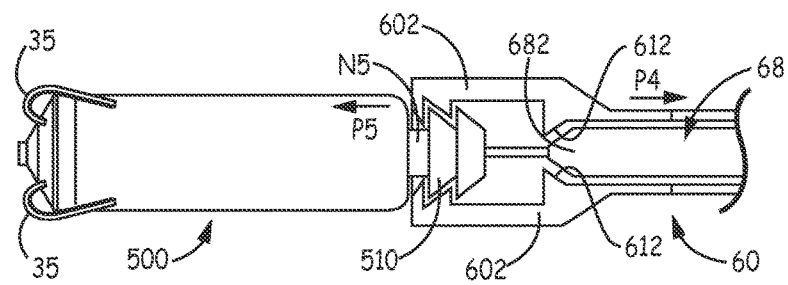

An operator may load device 500 into catheter 600 by first bringing a holding member 510 of device 500 into confronting engagement with distal-facing surfaces 622 of retention features 602, as illustrated in FIG. 6A, and then by pushing holding member 510 and retention features 602 against one another to elastically deform features 602 and expand second diameter D26 of distal opening 621 so that holding member 510 passes therethrough. With further reference to FIG. 6A, the gap defined by necked-in portion N5 of holding member 510, similar to that defined by necked-in portion N of holding member 310 of device 300, is between a head H5 of holding member 510 and device housing proximal end 381, so, once holding member head H5 passes through distal opening 621, retention features 602 relax back toward the constricted configuration that allows for an interlocking engagement of features 602 within the gap defined by necked-in portion N5, as illustrated in FIG. 6B. With reference back to FIG. 5C, a second distal-facing surface 622-2 of each retention feature 602 may conform to a contour of holding member head H5, for example, as shown in FIG. 6B, and head H5 of device holding member 510 may include another necked-in portion IN (FIG. 6A) that defines an intermediate gap within which retention features 602 also interlock, as shown in FIG. 6B.

Figure 6C:
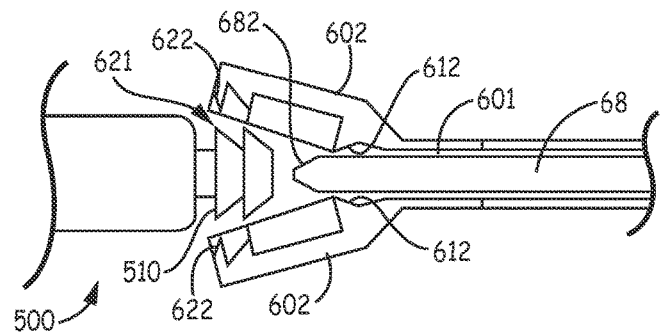

With further reference to FIGS. 5C and 6B, each retention feature 602 further includes a first proximal-facing surface 612 against which a distal tip 682 of an elongate release member 68 of the inner assembly of catheter 600, for example, a rod or mandrel in sliding engagement within inner assembly shaft lumen 601, may apply a push force, to move retention features 602 to a deformed condition, at which distal opening 621 of lumen 601 expands to an open configuration, to release device 500 from interlocking engagement, as shown in FIG. 6C. With reference back to FIG. 5A, release member 68, which is shown with dashed lines, may be coupled to control member 478 of handle proximal portion 472, similar to release member 48 of catheter 400, so that the operator may move release member 68 within lumen 601, per the double-headed arrow, via control member 478.

According to the illustrated embodiment of shaft distal end 62, retention features 602 have a ratchet-like configuration, and further include second and third a proximal-facing surfaces 612-2, 612-3 (FIG. 5C), wherein second proximal-facing surface 612-2 is located between first and second distal-facing surfaces 622, 622-2, and third proximal-facing surface 612-3 is located between second distal-facing surface 622-2 and first proximal-facing surface 612. Such a configuration is particularly suited to resist movement of features 602 toward the deformed condition, in response to a pull force applied to the engaged device 500, per arrow P4, or by device 500, per arrow P5 (FIG. 6B), that could prematurely release device 500 from the interlocking engagement thereof. According to an exemplary embodiment, distal end 62 of inner assembly shaft 60 may be formed from a relatively hard medical grade plastic, such as PEBAX® 7233, for example, being injection molded and then fused to the distal portion of shaft 60 by any suitable method known to those skilled in the art; and shaft 60 may be formed from braided stainless steel, or by one or more medical grade polymers, for example, one or more appropriate grades of polyether block amide, which are fused together and arranged for decreasing stiffness from handle proximal portion 472 to distal end 62 (e.g., including PEBAX® 7233, 6333, 4033, and 3533).

FIG. 7A is a plan view of an interventional medical system 7300, according to some additional embodiments of the present invention. System 7300 is shown including a catheter 700, which includes an inner assembly extending within the above-described elongate outer tubular member 45, and the above-described medical device 300, which is oriented so that device holding member 310 is directed toward a distal end 72 of a shaft 70 of the catheter inner assembly for engagement therewith in the loading of device 300 into catheter 700. FIG. 7A further illustrates catheter 700 including handle 47 that is described above. The distal end view of FIG. 7B and the longitudinal cross-section view of FIG. 7C (through section-line C-C of FIG. 7A) illustrate shaft distal end 72 including two pairs of opposing elastically deformable retention features 702 that protrude into a lumen 701 of shaft 70, wherein each retention feature 702 includes at least three retaining struts RS forming a distal facing surface 722, and at least one passageway strut PS forming a proximal-facing surface 712.

FIGS. 7B-C illustrate each retaining strut RS and passageway strut PS extending between a central end RS-c, PS-c thereof and a perimeter end RS-p, PS-p thereof, wherein each strut perimeter end RS-p, PS-p is secured to an inner surface of shaft distal end 72, and strut central ends RS-c, PS-c of each retention feature 702 are joined together at distal-facing surface 722 thereof. According to the illustrated embodiment, distal-facing surfaces 722 of retention features 702 define a distal opening 721 of shaft lumen 701 that is expandable via deformation of struts RS, PS, as will be described in greater detail below. FIGS. 7B-C further illustrate retaining strut perimeter ends RS-p of each retention feature 702 being co-planar and spaced apart from one another such that the outer ones of retaining struts RS define an angle β, which may be approximately 70 degrees. FIG. 7C further illustrates passageway strut perimeter end PS-p of each retention feature 702 being offset proximally from the corresponding retaining strut perimeter ends RS-p, such that passageway strut PS and the middle one of retaining struts RS enclose an angle φ, which may be approximately 45 degrees, in the illustrated un-deformed, or relaxed condition. (As was alluded to above, in some embodiments, each group of struts RS, PS may form the internal structure of each retention feature 402, wherein distal-facing surface 422 of each feature 402 may be supported by struts RS and proximal-facing surface 421 of each feature 402 supported by strut PS.)

Figure 7D:
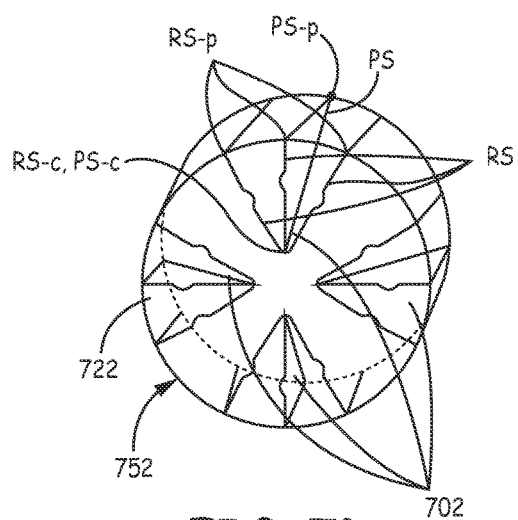
FIGS. 7D-E are perspective views of portions of the distal end of the catheter of the FIG. 7A system.
Figure 7E:
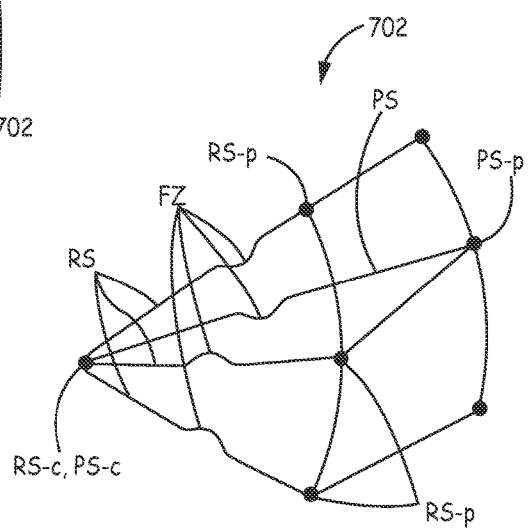

FIG. 7D is a perspective view of retention features 702 separate from catheter inner assembly shaft 70, in which the above described spacing of strut perimeter ends RS-p, PS-p can be better seen. According to some embodiments, strut perimeter ends RS-p, PS-p of retention features 702 may be connected together by a frame/ring 752 that extends within shaft distal end 72, for example, being heat bonded thereto. With reference to FIG. 7E, which is an enlarged perspective view of one of retention features 702, each strut RS, PS includes a flex zone FZ located between the corresponding perimeter end RS-p, PS-p and the corresponding central end RS-c, PS-c. According to an exemplary embodiment, each strut RS, PS may be formed from a shape-memory member, for example, a Nitinol wire or Polyglycolic acid (PGA) strand, wherein flex zone FZ is formed by a crimp in the shape-memory member. Each flex zone FZ allows for a buckling or stretching of the corresponding strut RS, PS when retention features 702 are moved into a deformed condition to expand distal opening 721 of shaft lumen 701 from the constricted configuration, which is shown in FIGS. 7B-C and 8B, to an open configuration, which is shown in FIGS. 8A and 8C.

Figure 8A:
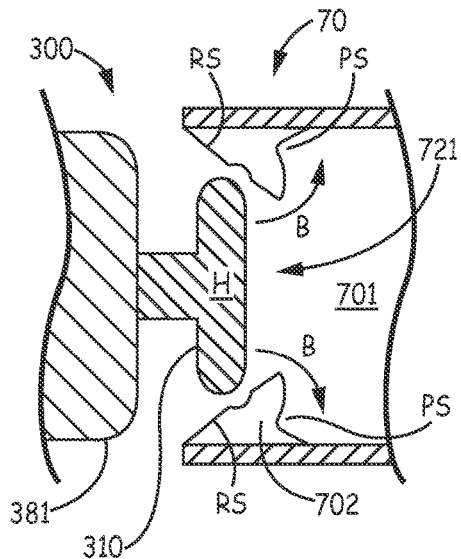
FIGS. 8A-C are cross-section views of portions of the medical device and the catheter of the FIG. 7A system, according to some embodiments and methods.
Figure 8B:
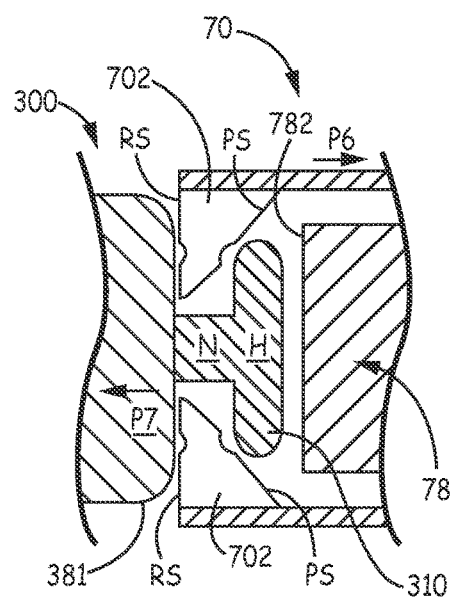

FIG. 8A illustrates the expansion of distal opening 721 of shaft lumen 701 when loading device 300 into catheter 700 so that retention features 702 of catheter inner assembly shaft 70 interlock with device holding member 310, as shown in FIG. 8B. With reference to FIG. 8A, the movement of retention features 702 to the deformed condition, at which distal opening 721 expands, per arrows B, is caused by bringing device holding member 310 and retention features 702 into confronting engagement, and then pushing holding member 310 and retention features 702 against one another until passageway struts PS buckle and retaining struts RS stretch. Once head H of device holding member 310 has passed through distal opening 721, retention features 702 relax back toward the constricted configuration that allows for an interlocking engagement of features 702 within the gap defined by necked-in portion N of device holding member 310, as illustrated in FIG. 8B. With reference back to FIG. 7A, to complete the loading of device 300 into catheter 700, the operator may advance outer tubular member 45, for example, by moving handle distal portion 475 per arrow A, relative to the catheter inner assembly, so that distal end 452 of outer tubular member 45 contains distal end 72 of the catheter inner assembly and the engaged device 300, for example, as shown in FIG. 9A.

Figure 8C:
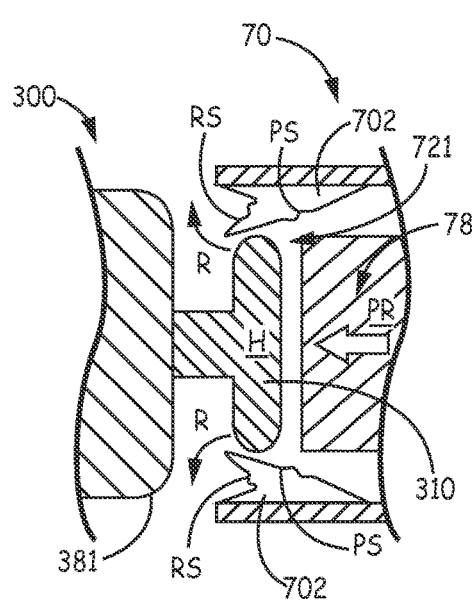

With reference back to FIG. 7C, the inner assembly of catheter 700, further includes an elongate release member 78, for example, a rod, configured to slide within shaft lumen 701 and to apply a push force against proximal-facing surfaces 712 of retention features 702, for example, to release the loaded device 300 from interlocking engagement with catheter inner assembly shaft 70, as shown in FIG. 8C. FIG. 8B illustrates a distal-most surface 782 of release member 78, which is configured to interface with a proximal-most surface of holding member head H, positioned within lumen 701 to apply a push force through holding member head H and against passageway struts PS, which form proximal-facing surfaces 712 of retention features 702 (FIG. 7C). With reference to FIG. 7A, and according to some embodiments, release member 78, which is represented with dashed lines, is coupled to control member 478, being movable in proximal and distal directions per the double-headed arrow. FIG. 8C illustrates the push force, per arrow PR, applied by release member 78 against retention features 702 to expand distal opening 721 of shaft lumen 701, per arrows R, by stretching passageway struts PS and buckling retaining struts RS, which releases device 300 from engagement with retention features 702. With further reference to FIG. 8B, retention features 702 are configured to resist deformation in a distal direction in response to a pull force applied through shaft 70, to the engaged device 300, per arrow P6, or by the engaged device 300, per arrow P7, for example, requiring a force four times greater to expand distal opening 721 in releasing device than that required to expand distal opening 721 to engage device.

Figure 9B:
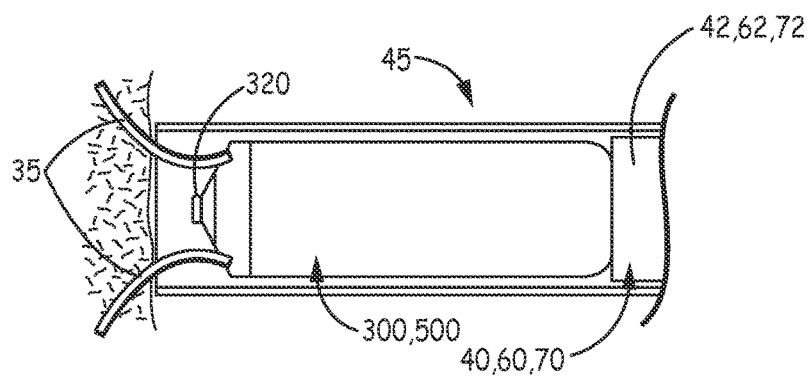
Figure 9C:
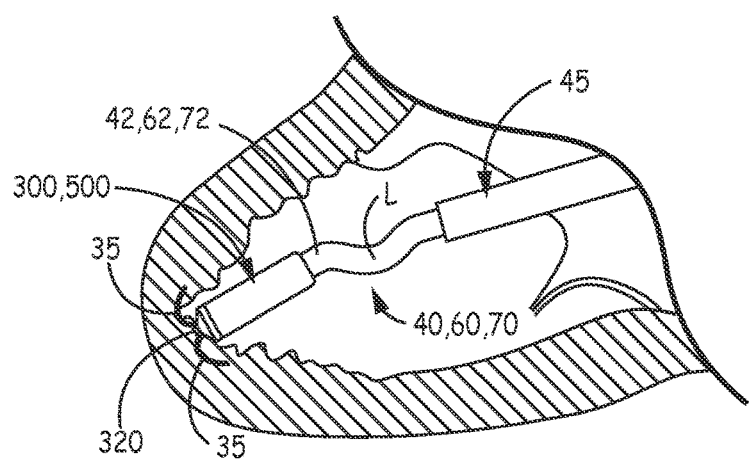

FIGS. 9A-C are schematics outlining some methods of the present invention. FIG. 9A illustrates a distal portion of catheter 400, 600, 700 into which relatively compact medical device 300, 500 is loaded for delivery to an implant site, such that device fixation fingers 35 are held in the extended condition within distal end 452 of outer tubular member 45. As was described above, the operator may first secure device 300, 500 to catheter inner assembly shaft 40, 60, 70 by bringing device holding member 310, 510 into confronting engagement with opposing retention features 402, 602, 702 (FIGS. 4A, 6A, 7A), and then by pushing holding member 310, 510 and retention features 402, 602, 702 against one another, to elastically deform features 402, 602, 702 and expand distal opening 421, 621, 721 of inner assembly shaft lumen 401, 601, 701, and to pass device holding member 310, 510 through the expanded distal opening 421, 621, 721 so that retention features 402, 602, 702 come into interlocking engagement therewith (FIGS. 4B, 6B, 7B). To complete the loading of device 300, 500, according to some methods, the operator moves outer tubular member 45 distally relative to shaft 40, 60, 70 and secured device 300, 500, from the above described retracted position (FIGS. 3A, 5A, 7A) to the advanced position, so that an entirety of device 300, 500 passes through distal-most opening 425 of outer tubular member 45. Once loaded, the operator advances catheter 400, 600, 700 within a patient's vascular system to position device fixation fingers 35 in proximity with an implant site, for example, any of the cardiac implant sites mentioned above in conjunction with FIG. 1. Once positioned, the operator may then apply a push force through inner assembly shaft 40, 60, 70 to engage device fixation fingers 35 with tissue at the implant site, for example, as shown in FIG. 9B. With further reference to FIG. 9B, according to those methods in which the operator moved outer tubular member 45 to the advanced position, to complete the loading of device 300, 500, the operator subsequently moves outer tubular member 45 proximally, back toward the retracted position to expose device fixation fingers 35 at the implant site, for example, while applying the push force through shaft 40, 60. Once device fixation fingers 35 are engaged, so that electrode 320 is brought into intimate contact with tissue at the implant site, the operator may release device 300, 500 from interlocking engagement with shaft retention features 402, 602, 702, for example, as described above in conjunction with FIGS. 4C, 6C, and 7C. But, according to some methods, the operator may evaluate device electrical performance before releasing device 300, 500, for example as shown in FIG. 9C. With reference to FIG. 9C, before evaluating the device performance, the operator may retract outer tubular member 45, relative to shaft 40, 60, 70 and secured device 300, 500, a sufficient distance so that a stiffness of tubular member 45 will not influence the contact between electrode 320 and the implant site tissue. According to some embodiments, inner assembly shaft 40, 60, 70 includes a relatively limp zone L extending proximally from distal end 42, 62, which is more flexible that distal end 42, 62, and sufficiently flexible so that a stiffness of shaft 40, 60, 70 will not influence the contact between electrode 320 and tissue.

Figure 10:
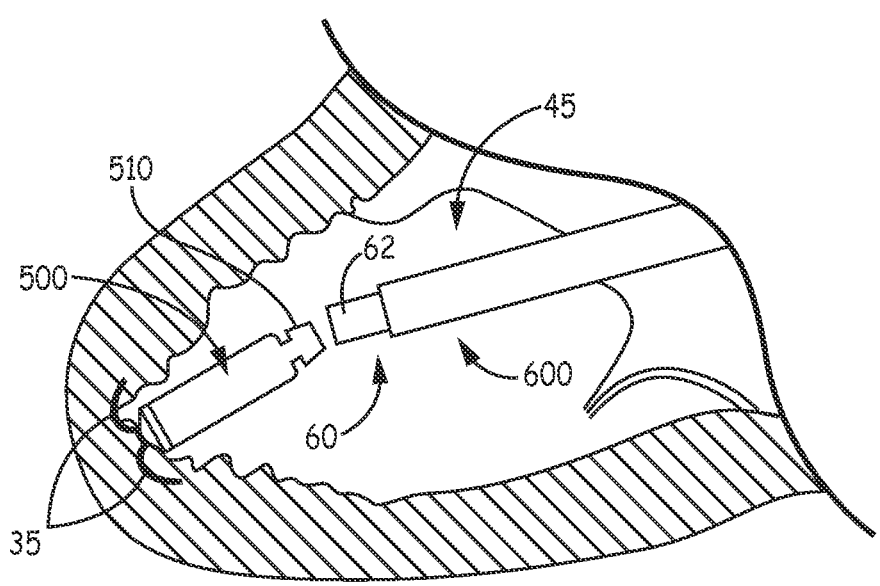

With reference to the schematic of FIG. 10, if, after the operator releases device 500, the operator desires to retrieve implanted device 500 from the implant site, the operator may employ catheter 600. According to some methods, after positioning catheter 600 in proximity to implanted device 500, with outer tubular member in the retracted position, as shown in FIG. 10, the operator may apply a push force against proximal-surfaces 612 of opposing retention features 602, via release member 68, to expand distal opening 621 of shaft lumen 601, for example, as described above in conjunction with FIG. 6C. Then the operator can advance catheter 600 to position the expanded distal opening 621 of retention features 602 around device holding member 510, as shown in FIG. 6C, after which, the operator retracts release member 68 so that distal opening 621 is allowed to constrict, and retention features 602 interlock with holding member 510, as described above and shown in FIG. 6B. Once in interlocking engagement with device holding member 510, the operator may apply a pull force through shaft 60 to disengage device fixation fingers 35 from the implant site, and, either during or after applying the pull force, move outer tubular member 45 distally, relative to shaft 60, to the advanced position thereof, so that an entirety of device 500 passes through distal-most opening 425 of outer tubular member 45 to be contained therein, as shown in FIG. 9A.

According to some alternate methods, the operator may employ catheter 400, 700 to retrieve device 300 from an implant site, for example, by positioning distal end 42, 72 of shaft 40, 70 in proximity to device holding member 310 and then bringing opposing retention features 402, 702 into confronting engagement therewith, as shown in FIG. 4A, 7A. Then, when the operator applies a push force through shaft 40, 70, device holding member 310 deforms retention features 402, 702 and expands distal opening 421, 721 of shaft lumen 401, 701, thereby allowing passage of holding member 310 through opening 421, 721 and into interlocking engagement with features 402, 702, as shown in FIG. 4B, 7B. Once in interlocking engagement with device holding member 310, the operator may apply a pull force through shaft 40, 70 to disengage device fixation fingers 35 from the implant site, either before or while moving outer tubular member 45 distally to the advanced to contain device 300, as shown in FIG. 9A.

In the foregoing detailed description, the invention has been described with reference to specific embodiments. However, it may be appreciated that various modifications and changes can be made without departing from the scope of the invention as set forth in the appended claims. For example, the following Items are illustrative of further embodiments:

Item 1. An interventional medical system comprising a relatively compact implantable medical device and a catheter; the medical device comprising an electronic controller, a hermetically sealed housing containing the controller, an electrode electrically coupled to the controller and mounted in proximity to a distal end of the housing, a fixation member mounted to the distal end of the housing, and a holding member joined to a proximal end of the housing and protruding proximally therefrom, the holding member including a head and a necked-in portion that defines a gap between the head and the proximal end of the housing; the catheter comprising an elongate inner assembly and an elongate outer tubular member, the outer tubular member including an elongate lumen extending along a length thereof and including a distal-most opening formed at a distal end of the outer tubular member, the distal-most opening allowing passage of the medical device therethrough, and the inner assembly extending along, and being in sliding engagement within the lumen of the outer tubular member; and the catheter inner assembly comprising:

an elongate shaft including a distal end and an elongate lumen, the distal end of the shaft comprising opposing elastically deformable retention features that protrude into the shaft lumen, each retention feature including a distal-facing surface and a proximal-facing surface, the distal-facing surfaces defining a distal opening of the shaft lumen, the distal opening being expandable from a constricted configuration to an open configuration by moving the retention features from a relaxed condition to a deformed condition, respectively, the open configuration allowing passage of the device holding member through the distal opening of the shaft lumen, and the constricted configuration allowing for an interlocking engagement of the retention features within the gap defined by the necked-in portion of the device holding member; and an elongate release member configured to slide within the shaft lumen and to apply a push force against the proximal-facing surfaces of the shaft retention features, the push force moving the retention features to the deformed condition to expand the distal opening of the shaft lumen from the constricted to the open configuration; and wherein the outer tubular member of the catheter is movable between a retracted position and an advanced position, the distal end of the inner assembly shaft being exposed distal to the distal-most opening of the outer tubular member when the outer tubular member is in the retracted position, and the distal end of the inner assembly shaft being contained within the lumen of the outer tubular member when the outer tubular member is in the advanced position.

Item 2. The system of item 1, wherein the distal opening of the catheter inner assembly shaft lumen tapers from a first, distal-most diameter to a second diameter, the first diameter being greater than the second diameter, and the second diameter being expandable from the constricted configuration to the open configuration.

Item 3. The system of item 2, wherein the first, distal-most diameter of the distal opening of the catheter inner assembly shaft lumen is approximately maintained when the retention features are moved to the deformed condition to expand the second diameter of the distal opening of the catheter inner assembly shaft lumen.

Item 4. The system of item 2, wherein the first, distal-most diameter of the distal opening of the catheter inner assembly shaft lumen also expands when retention features are moved to the deformed condition to expand the second diameter of the distal opening of the catheter inner assembly shaft lumen.

Item 5. The system of any one of items 1-4, wherein the elongate release member of the catheter inner assembly comprises a tube, the tube including a distal-most edge configured to push against the proximal-facing surfaces of the shaft retention features.

Item 6. The system of any one of items 1-5, wherein the shaft of the catheter inner assembly includes two pairs of the opposing elastically deformable retention features, each retention feature including free edges that extend within the shaft lumen, and the free edges of adjacent retention features extending alongside and in close proximity with one another within the shaft lumen, when the retention features are in the relaxed condition.

Item 7. The system of any one of items 1-6, wherein the elongate release member of the catheter inner assembly comprises a rod, the rod including a distal-most surface configured to interface with a proximal-most surface of the device holding member, such that the release member applies the push force against the proximal-facing surfaces of the shaft retention features through the holding member.

Item 8. The system of any one of items 1-7, wherein the elongate release member of the catheter inner assembly comprises a rod, the rod including a distal tip configured to apply the push force against the proximal-facing surfaces of the shaft retention features.

Item 9. The system of any one of items 1-8, wherein the distal-facing surface of each retention feature of the catheter inner assembly shaft is a first of at least two distal-facing surfaces thereof, a second of the at least two distal-facing surfaces being located between the first distal-facing surface and the proximal-facing surface, the second distal-facing surface conforming to a contour of the head of the device holding member, when the retention features are in interlocking engagement within the gap defined by the necked-in portion of the device holding member.

Item 10. The system of any one of items 1-9, wherein
the distal-facing surface of each retention feature of the catheter inner assembly shaft is a first of at least two distal-facing surfaces thereof, a second of the at least two distal-facing surfaces being spaced proximally apart from the first distal-facing surface;
the proximal-facing surface of each retention feature of the catheter inner assembly shaft is a first of three proximal-facing surfaces thereof, a second of the three proximal-facing surfaces being located between the first and second distal-facing surfaces, and a third of the three proximal-facing surfaces being located between the second distal-facing surface and the first proximal-facing surface;
the holding member of the medical device includes another necked-in portion spaced proximally from the necked-in portion that defines the gap between the holding member and the proximal end of the housing, the other necked-in portion defining an intermediate gap of the device holding member; and
the retention features also interlock within the intermediate gap of the device holding member when the features are in interlocking engagement within the gap between the device holding member and the proximal end of the device housing.

Item 11. The system of any one of items 1-10, wherein the shaft of the catheter inner assembly further includes a relatively limp zone extending proximally from the distal end of the shaft, the relatively limp zone being more flexible than the distal end of the shaft.

Item 12. The system of any one of items 1-11, wherein:
the shaft of the catheter inner assembly includes two pairs of the opposing elastically deformable retention features, each retention feature comprising at least three retaining struts and at least one passageway strut, the retaining struts forming or supporting the distal-facing surface of the corresponding retention feature, and the passageway strut forming or supporting the proximal-facing surface of the corresponding retention feature;
each retaining strut and passageway strut of each retention feature includes a perimeter end and a central end, each perimeter end being secured to an inner surface of the shaft distal end, the central ends of the struts of each retention feature being joined together at the distal-facing surface thereof, the perimeter ends of the at least three retaining struts of each retention feature being co-planar and spaced apart from one another, and the perimeter end of the at least one passageway strut of each retention feature being offset proximally from the perimeter ends of the corresponding retaining struts; and
each retaining strut and passageway strut includes a flex zone located between the perimeter and central ends thereof.

Item 13. The system of item 12, wherein:
each of the retaining and passageway struts of the opposing elastically deformable retention features comprises a shape-memory member; and
a crimp in each shape-memory member forms the flex zone of the corresponding strut.

Item 14. The system of item 12, wherein the elongate release member of the catheter inner assembly comprises a rod, the rod including a distal-most surface configured to interface with a proximal-most surface of the head of the device holding member, such that the release member applies the push force against the proximal-facing surfaces of the shaft retention features through the holding member.

Item 15. A method for delivering a relatively compact implantable medical device to an implant site within a patient's vascular system, the method comprising:
loading the medical device into a catheter, the loading comprising:
bringing a holding member of the medical device into confronting engagement with opposing retention features, the opposing retention features comprising a distal end of a shaft of the catheter and defining a distal opening of a lumen of the shaft, the device holding member being joined to a proximal end of a housing of the medical device and protruding proximally therefrom, the holding member including a necked-in portion that defines a gap between the holding member and the proximal end of the housing; and
pushing the confronting device holding member and the catheter shaft retention features against one another to elastically deform the opposing retention features and expand the distal opening of the shaft lumen, and to pass the device holding member through the expanded distal opening and into the lumen so that the retention features come into an interlocking engagement within the gap defined by the necked-in portion of the holding member;

advancing the catheter and the loaded device within the patient's vascular system to position a fixation member of the device in close proximity to the implant site, the device fixation member being mounted to a distal end of the device housing;

engaging the positioned device fixation member with tissue at the implant site by applying a push force through the catheter shaft; and releasing the medical device from the interlocking engagement of the catheter shaft retention features, after engaging the positioned device fixation member, by applying a push force against proximal-facing surfaces of the catheter shaft retention features, the push force being applied through an elongate release member that extends within the catheter shaft lumen, and the push force elastically deforming the retention features to expand the distal opening of the lumen.

Item 16. The method of item 15, wherein loading the medical device further comprises moving an outer tubular member of the catheter distally relative to the catheter shaft, from a retracted position to an advanced position, the retracted position being that at which the catheter shaft distal end is exposed distal to a distal-most opening of a lumen of the outer tubular member, and the advanced position being that at which the lumen of the tubular member contains the loaded medical device therein; and further comprising moving the outer tubular member proximally relative to the loaded medical device, toward the retracted position, to expose the device fixation member, after advancing the catheter and the loaded device, and while engaging the positioned device fixation member with the tissue at the implant site.

Item 17. The method of item 15, further comprising:

positioning a portion of the elongate release member along a relatively limp zone of the catheter shaft, to stiffen the limp zone for applying the push force through the catheter shaft to engage the positioned device fixation member, the limp zone extending proximally from the distal end of the catheter shaft;

retracting the portion of the release member out from the limp zone of the catheter shaft, after engaging the positioned device fixation member with the tissue at the implant site, and before releasing the device; and evaluating a performance of the device, when the positioned device fixation member is engaged with the tissue at the implant site, after retracting the portion of the release member out from the limp zone of the catheter shaft, and before releasing the device.

Item 18. A method for retrieving a relatively compact implanted medical device from an implant site in a patient's vascular system, the method comprising:

positioning a catheter in the patient's vascular system so that opposing retention features thereof are in proximity to a holding member of the implanted device, the opposing retention features comprising a distal end of a shaft of the catheter and defining a distal opening of a lumen of the shaft, the device holding member being joined to a proximal end of a housing of the medical device and protruding proximally therefrom, the holding member including a necked-in portion that defines a gap between the holding member and the proximal end of the housing;

applying a push force against proximal-facing surfaces of the catheter shaft retention features, the push force being applied through an elongate release member that extends within the catheter shaft lumen, and the push force elastically deforming the retention features to expand the distal opening of the lumen;

positioning the expanded distal opening of the catheter shaft lumen around the holding member of the implanted medical device;

retracting the release member, after positioning the expanded distal opening of the catheter shaft lumen, so that the distal end of the release member no longer pushes against the proximal-facing surfaces of the retention features, thereby allowing the distal opening of the catheter shaft lumen to constrict so that the retention features interlock within the gap defined by the necked-in portion of the device holding member; and applying a pull force through the catheter shaft, after retracting the release member, to disengage a fixation member of the device from tissue at the implant site, the fixation member being mounted to a distal end of the device housing.

Item 19. The method of item 18, further comprising moving an outer tubular member of the catheter distally relative to the catheter shaft, from a retracted position to an advanced position, either during or after applying the pull force, the retracted position being that at which the catheter shaft distal end is exposed distal to a distal-most opening of a lumen of the outer tubular member, and the advanced position being that at which the lumen of the tubular member contains the device therein.

We claim:

1. An interventional medical system comprising a relatively compact implantable medical device and a catheter; the medical device comprising a hermetically sealed housing, an electrode mounted in proximity to a distal end of the housing, a fixation member mounted to the distal end of the housing, and a holding member joined to a proximal end of the housing and protruding proximally therefrom, the holding member including a head and a necked-in portion that defines a gap between the head and the proximal end of the housing; the catheter comprising an elongate inner assembly and an elongate outer tubular member, the outer tubular member including an elongate lumen extending along a length thereof and including a distal-most opening formed at a distal end of the outer tubular member, the distal-most opening allowing passage of the medical device therethrough, and the inner assembly extending along, and being in sliding engagement within the lumen of the outer tubular member; and the catheter inner assembly comprising:

an elongate shaft including a distal end and an elongate lumen, the distal end of the shaft comprising opposing elastically deformable retention features that protrude into the shaft lumen, each retention feature including a distal-facing surface and a proximal-facing surface, the distal-facing surfaces defining a distal opening of the shaft lumen, the distal opening being expandable from a constricted configuration to an open configuration by moving the retention features from a relaxed condition to a deformed condition, respectively, the open configuration allowing passage of the device holding member through the distal opening of the shaft lumen, and the constricted configuration allowing for an interlocking engagement of the retention features within the gap defined by the necked-in portion of the device holding member; and an elongate release member configured to slide within the shaft lumen and to apply a push force against the proximal-facing surfaces of the shaft retention features, the push force moving the retention features to the deformed condition to expand the distal opening of the shaft lumen from the constricted to the open configuration; and wherein the outer tubular member of the catheter is movable between a retracted position and an advanced position, the distal end of the inner assembly shaft being exposed distal to the distal-most opening of the outer tubular member when the outer tubular member is in the retracted position, and the distal end of the inner assembly shaft being contained within the lumen of the outer tubular member when the outer tubular member is in the advanced position.

2. The system of claim 1, wherein the distal opening of the catheter inner assembly shaft lumen tapers from a first, distal-most diameter to a second diameter, the first diameter being greater than the second diameter, and the second diameter being expandable from the constricted configuration to the open configuration.

3. The system of claim 2, wherein the first, distal-most diameter of the distal opening of the catheter inner assembly shaft lumen is approximately maintained when the retention features are moved to the deformed condition to expand the second diameter of the distal opening of the catheter inner assembly shaft lumen.

4. The system of claim 2, wherein the first, distal-most diameter of the distal opening of the catheter inner assembly shaft lumen also expands when retention features are moved to the deformed condition to expand the second diameter of the distal opening of the catheter inner assembly shaft lumen.

5. The system of claim 1, wherein the elongate release member of the catheter inner assembly comprises a tube, the tube including a distal-most edge configured to push against the proximal-facing surfaces of the shaft retention features.

6. The system of claim 1, wherein the shaft of the catheter inner assembly includes two pairs of the opposing elastically deformable retention features, each retention feature including free edges that extend within the shaft lumen, and the free edges of adjacent retention features extending alongside and in close proximity with one another within the shaft lumen, when the retention features are in the relaxed condition.

7. The system of claim 1, wherein the elongate release member of the catheter inner assembly comprises a rod, the rod including a distal-most surface configured to interface with a proximal-most surface of the device holding member, such that the release member applies the push force against the proximal-facing surfaces of the shaft retention features through the holding member.

8. The system of claim 1, wherein the elongate release member of the catheter inner assembly comprises a rod, the rod including a distal tip configured to apply the push force against the proximal-facing surfaces of the shaft retention features.

9. The system of claim 1, wherein the distal-facing surface of each retention feature of the catheter inner assembly shaft is a first of at least two distal-facing surfaces thereof, a second of the at least two distal-facing surfaces being located between the first distal-facing surface and the proximal-facing surface, the second distal-facing surface conforming to a contour of the head of the device holding member, when the retention features are in interlocking engagement within the gap defined by the necked-in portion of the device holding member.

10. The system of claim 1, wherein the distal-facing surface of each retention feature of the catheter inner assembly shaft is a first of at least two distal-facing surfaces thereof, a second of the at least two distal-facing surfaces being spaced proximally apart from the first distal-facing surface;

the proximal-facing surface of each retention feature of the catheter inner assembly shaft is a first of three proximal-facing surfaces thereof, a second of the three proximal-facing surfaces being located between the first and second distal-facing surfaces, and a third of the three proximal-facing surfaces being located between the second distal-facing surface and the first proximal-facing surface;

the holding member of the medical device includes another necked-in portion spaced proximally from the necked-in portion that defines the gap between the holding member and the proximal end of the housing, the other necked-in portion defining an intermediate gap of the device holding member; and the retention features also interlock within the intermediate gap of the device holding member when the features are in interlocking engagement within the gap between the device holding member and the proximal end of the device housing.

11. The system of claim 1, wherein the shaft of the catheter inner assembly further includes a relatively limp zone extending proximally from the distal end of the shaft, the relatively limp zone being more flexible than the distal end of the shaft.

12. The system of claim 1, wherein:

the shaft of the catheter inner assembly includes two pairs of the opposing elastically deformable retention features, each retention feature comprising at least three retaining struts and at least one passageway strut, the retaining struts forming or supporting the distal-facing surface of the corresponding retention feature, and the passageway strut forming or supporting the proximal-facing surface of the corresponding retention feature;

each retaining strut and passageway strut of each retention feature includes a perimeter end and a central end, each perimeter end being secured to an inner surface of the shaft distal end, the central ends of the struts of each retention feature being joined together at the distal-facing surface thereof, the perimeter ends of the at least three retaining struts of each retention feature being co-planar and spaced apart from one another, and the perimeter end of the at least one passageway strut of each retention feature being offset proximally from the perimeter ends of the corresponding retaining struts; and each retaining strut and passageway strut includes a flex zone located between the perimeter and central ends thereof.

13. The system of claim 12, wherein:

each of the retaining and passageway struts of the opposing elastically deformable retention features comprises a shape-memory member; and a crimp in each shape-memory member forms the flex zone of the corresponding strut.

14. The system of claim 12, wherein the elongate release member of the catheter inner assembly comprises a rod, the rod including a distal-most surface configured to interface with a proximal-most surface of the head of the device holding member, such that the release member applies the push force against the proximal-facing surfaces of the shaft retention features through the holding member.

* * * * *